United States Patent [19]

Natarajan et al.

[11] 4,206,122
[45] Jun. 3, 1980

[54] DERIVATIVES OF PYRROLIDINECARBOXALDEHYDE AND PIPERIDINECARBOXALDEHYDE AND INTERMEDIATES THEREFOR

[75] Inventors: Sesha I. Natarajan, Lawrenceville; Miguel A. Ondetti, Princeton, both of N.J.

[73] Assignee: E. R. Squibb & Sons, Inc., Princeton, N.J.

[21] Appl. No.: 896,420

[22] Filed: Apr. 14, 1978

[51] Int. Cl.² .................. A61K 31/40; C07D 207/04
[52] U.S. Cl. .................. 260/326.25; 260/326.5 S; 546/188; 546/189; 546/208; 546/242; 546/245; 424/267; 424/274
[58] Field of Search .................. 260/293.63, 293.71, 260/293.85, 326.5 S, 326.25; 546/188, 189, 208, 242, 245

[56] References Cited

U.S. PATENT DOCUMENTS

| | | | |
|---|---|---|---|
| 4,046,889 | 9/1977 | Ondetti | 424/244 |
| 4,105,776 | 8/1978 | Ondetti | 424/274 |

*Primary Examiner*—Donald G. Daus
*Assistant Examiner*—Lisa Jones
*Attorney, Agent, or Firm*—Lawrence S. Levinson; Merle J. Smith; Stephen B. Davis

[57] ABSTRACT

Derivatives of pyrrolidinecarboxaldehyde and piperidinecarboxaldehyde, and intermediates therefor, which have the general formula

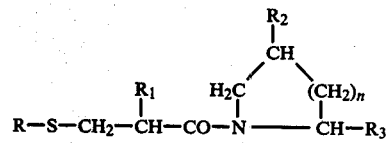

wherein R is hydrogen, lower alkanoyl or

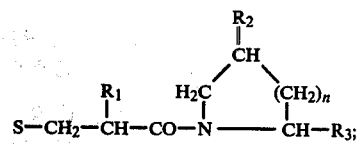

$R_1$ is hydrogen or lower alkyl;
$R_2$ is hydrogen or hydroxy;
$R_3$ is hydroxymethyl, di(lower alkoxy)methyl or formyl;
n is 1 or 2;

and their bisulfite addition products, are useful as hypotensive agents.

21 Claims, No Drawings

DERIVATIVES OF PYRROLIDINECARBOXALDEHYDE AND PIPERIDINECARBOXALDEHYDE AND INTERMEDIATES THEREFOR

SUMMARY OF THE INVENTION

This invention relates to new compounds which have the general formula

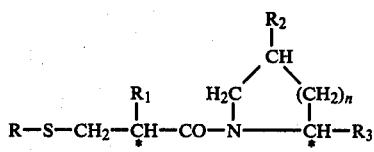

wherein R is hydrogen, lower alkanoyl or

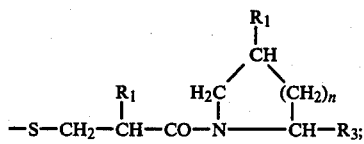

$R_1$ is hydrogen or lower alkyl;
$R_2$ is hydrogen or hydroxy;
$R_3$ is hydroxymethyl, di(lower alkoxy)methyl or formyl;
n is 1 or 2;
and their bisulfite addition products.

The asterisks indicate asymmetric carbon atoms.

DETAILED DESCRIPTION OF THE INVENTION

The invention in its broadest aspects relates to derivatives of pyrrolidine-2-carboxyaldehyde and piperidine-2-carboxaldehyde and to intermediates therefor.

Preferred are those compounds of formula I wherein R is acetyl, $R_1$ is hydrogen or lower alkyl, especially hydrogen or methyl; $R_2$ is hydrogen; $R_3$ is hydroxymethyl or formyl, especially formyl, and n is 1 or 2, especially 1.

The L-configuration for the pyrrolidine- or piperidine- substituted moiety is especially preferred.

The lower alkyl groups represented by $R_1$ include straight and branched chain hydrocarbon radicals from methyl to heptyl, for example, methyl, ethyl, propyl, isopropyl, butyl, isobutyl, t-butyl, pentyl, isopentyl and the like. The $C_1$–$C_4$ members, especially $C_1$ and $C_2$ members, are preferred.

The lower alkanol groups are those having the acyl radicals of the lower ($C_2$–$C_7$) fatty acids, for example, acetyl, propionyl, butyryl and the like. Similarly, those lower alkanoyl groups having up to four carbons, and especially acetyl, are preferred.

A preferred method for the synthesis of the compounds of formula I is the oxidation of the intermediate alcohol having the formula

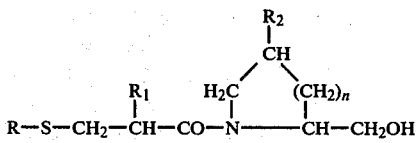

wherein the symbols have the same meaning as above,
with manganese dioxide, dimethylsulfoxide/dicyclohexylcarbodiimide, chromium trioxide/pyridine, etc. The procedure of oxidation utilizing dimethylsulfoxide/dicyclohexylcarbodiimide is preferred.

The intermediates of formula II are synthesized by coupling the acid of the formula

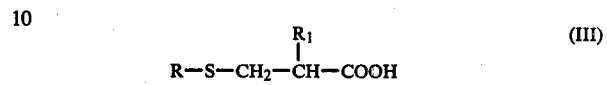

with an amino alcohol of the formula

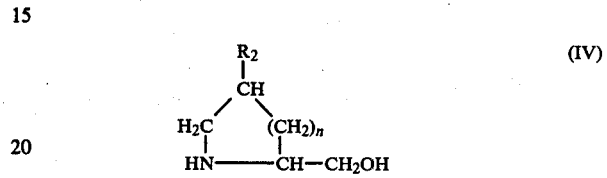

by any method which can be used to form amide bonds. See, for example, "Methoden der Organischen Chemie" (Houben-Weyl) part I, p. 736 et seq., part II, p. 1 et seq. (1974). The active ester method, e.g., using the nitrophenyl ester is preferred.

An alternate method is acylating with an acid of formula III the dialkyl acetal derivative of the formula

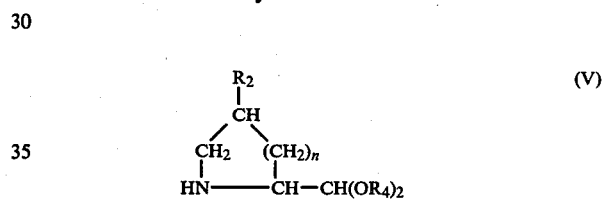

wherein $R_4$ is lower alkyl and $R_2$ is defined as above, to give a compound of the formula

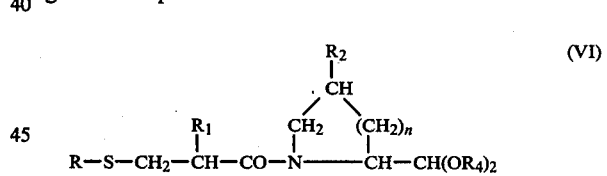

The compound of formula VI can be hydrolyzed to the compound of formula I wherein $R_3$ is formyl. The compound of formula VI can also be prepared from the compound of formula I ($R_3$ is formyl) by acetalization with a lower alkanol and acid.

The compounds of formula II wherein R is

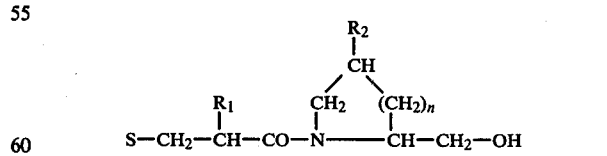

are obtained by oxidation of a compound of formula II wherein R is hydrogen with iodine.

The aldehydes of formula I, i.e., wherein $R_3$ is formyl, form bisulfite addition products with metal bisulfites principally the alkali metal bisulfites like sodium bisulfite, potassium bisulfite, etc. These can be characterized by the formula

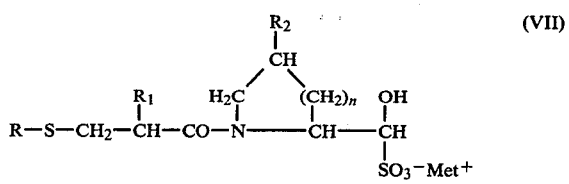

wherein Met represents the metal ion, e.g., sodium or potassium. Although these bisulfite addition products also have the hypotensive activity discussed below, they are principally useful to isolate the aldehydes in pure form and to characterize the products.

The products of formula I have asymmetric carbon atoms which are indicated by the asterisks. The compounds accordingly exist in stereoisomeric forms or in racemic mixtures thereof. All of these are within the scope of the invention. The above described syntheses can utilize the racemate or one of the enantiomers as starting material. When the racemic starting material is used in the synthetic procedure, the stereoisomers obtained in the product can be separated by conventional chromatographic or fractional crystallization methods. In general, the L-isomer with respect to the carbon of the heterocycle constitutes the preferred isomeric form.

The compounds of this invention are useful as hypotensive agents. They inhibit the conversion of the decapeptide angiotensin I to angiotensin II and therefore are useful in reducing or relieving angiotensin related hypertension. The action of the enzyme renin on angiotensinogen, a pseudoglobulin in blood plasma, produces angiotensin I. Angiotensin I is converted by angiotensin converting enzyme (ACE) to angiotensin II. The latter is an active pressor substance which has been implicated as the caustive agent in various forms of hypertension in various mammalian species, e.g., rats and dogs. The compounds of this invention intervene in the angiotensinogen→(renin)→angiotensin I→(ACE)→angiotensin II sequence by inhibiting angiotensin converting enzyme and reducing or eliminating the formation of the pressor substance angiotensin II. Thus by the administration of a composition containing one or a combination of compounds of formula I or a physiologically acceptable salt thereof, angiotensin dependent hypertension in the species of mammal suffering therefrom is alleviated. A single dose, or preferably two to four divided daily doses, provided on a basis of about 0.1 to 100 mg. per kilogram per day, preferably about 1 to 50 mg. per kilogram per day is appropriate to reduce blood pressure as indicated in the animal model experiments described by S. L. Engel, T. R. Schaeffer, M. H. Waugh and B. Rubin, Proc. Soc. Exp. Biol. Med. 143, 483(1973). The substance is preferably administered orally, but parenteral routes such as subcutaneously, intramuscularly, intravenously or intraperitoneally can also be employed. The alcohols of formula II have this activity but are not potent compounds and are useful when only mildly active compounds utilizing dosages at the highest end of the range above are desired. They are therefore principally useful as intermediates or to purify or isolate a product.

The compounds of this invention can be utilized to achieve the reduction of blood pressure by formulating in compositions such as tablets, capsules or elixirs for oral administration or in sterile solutions or suspensions for parenteral administration. About 10 to 500 mg. of a compound or mixture of compounds of formula I is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The following examples are illustrative of the invention and constitute especially preferred embodiments. All temperatures are in degrees Celsius.

EXAMPLE 1

3-(Acetylthio)propanoic acid p-nitrophenyl ester

To a stirred ice cold solution of ethyl acetate (75 ml.) containing 3-(acetylthio)propanoic acid (7.4 g. 50 mmol.) and p-nitrophenol (8.4 g., 60 mmol.) dicyclohexylcarbodiimide (10.3 g., 50 mmol.) is added in portions. After thirty minutes, the ice bath is removed and the solution stirred at room temperature overnight. The precipitated dicyclohexylurea is filtered off, ethyl acetate evaporated, and the residue dissolved in ethanol. The 3-(acetylthio)propanoic acid p-nitrophenyl ester crystallizes out, yield 8.6 g. (63.7%), m.p. 71°–73°.

EXAMPLE 2

1-(3-Acetylthiopropanoyl)-2-L-(hydroxymethyl)pyrrolidine

L-Prolinol is prepared according to the procedure described in J. Org. Chem., 32 2388 (1967).

A solution of L-prolinol (2.25 g., 22.5 mmol.) and 3-(acetylthio)propanoic acid p-nitrophenyl ester (6.4 g., 25 mmol.) in dimethylformamide (45 ml.) is kept at room temperature for six hours. The dimethylformamide is evaporated and the residual 1-(3-acetylthiopropanoyl)-2-L-(hydroxymethyl)pyrrolidine is chromatographed over silica gel (400 g., Mallinckrodt, SilicAR CC-7) using benzene:acetone (1:9) for elution. Yield 4.6 g. (88%), $R_f$=0.17, silica gel, benzene:acetone (4:1).

EXAMPLE 3

1-(3-Acetylthiopropanoyl)-2-L-pyrrolidinecarboxaldehyde

To a solution of 1-[3-acetylthiopropanoyl-2-L-(hydroxymethyl)pyrrolidine (1.84 g.) in DMSO (10.6 ml.), a benzene solution (10 ml.) containing pyridine (0.64 ml.) and trifluoroacetic acid (0.32 ml.) is added. Dicyclohexylcarbodiimide (4.96 g.) is added to this mixture in portions. After keeping the solution at room temperature for sixteen hours, it is diluted with ether (200 ml.) followed by the addition of a solution of oxalic acid (2.2 g.) in methanol (5 ml.). After thirty minutes, the solution is filtered to remove the precipitated dicyclohexylurea. The ethereal solution is concentrated and redissolved in toluene (10 ml.) when a small portion oils out. The toluene solubles are chromatographed over silica gel (150 g., Mallinckrodt, SilicAR CC-7) using 7% acetone in toluene for elution. Yield of 1-(3-acetylthiopropanoyl-2-L-pyrrolidinecarboxaldehyde 1.2 g., silica gel, $R_f$=0.33 (benzene:acetone, 4:1). $[\alpha]_D^{25}$ −103° (c=1.5, CHCl$_3$).

EXAMPLE 4

3-(Acetylthio)-2-methylpropanoic acid p-nitrophenyl ester

By substituting 3-acetylthio-2-methylpropanoic acid for the 3-acetylthiopropanoic acid in the procedure of Example 1, 3-acetylthio-2-methylpropanoic acid p-nitrophenyl ester is obtained.

EXAMPLE 5

1-(3-Acetylthio)-2-methylpropanoyl)-2-L-hydroxymethylpyrrolidine

By substituting 3-acetylthio-2-methylpropanoic acid p-nitrophenyl ester for the 3-acetylthiopropanoic acid p-nitrophenyl ester in the procedure of Example 2, 1-(3-acetylthio-2-methylpropanoyl)-2-L-hydroxymethylpyrrolidine is obtained.

EXAMPLE 6

1-(3-Acetylthio-2-methylpropanoyl)-2-L-pyrrolidinecarboxaldehyde

By substituting 1-(3-acetylthio-2-methylpropanoyl)-2-L-hydroxymethylpyrrolidine for the 1-(3-acetylthiopropanoyl)-2-L-hydroxymethylpyrrolidine in the procedure of Example 3, 1-(3-acetylthio-2-methylpropanoyl)-2-L-pyrrolidinecarboxaldehyde is obtained.

EXAMPLE 7

1-(3-Acetylthiopropanoyl)-2-DL-hydroxymethylpiperidine

By substituting 2-DL-hydroxymethylpiperidine [prepared from DL-pipecolic acid by the procedure described in J. Org. Chem. 32, 2388 (1976) for the preparation of L-prolinol] for the L-prolinol in the procedure of Example 2, 1-(3-acetylthiopropanoyl)-2-DL-hydroxymethylpiperidine is obtained.

EXAMPLE 8

1-(3-Acetylthiopropanoyl)-2-DL-piperidinecarboxaldehyde

By substituting 1-(3-acetylthiopropanoyl)-2-DL-hydroxymethylpiperidine for the 1-(3-acetylthiopropanoyl)-2-L-hydroxymethylpyrrolidine in the procedure of Example 3, 1-(3-acetylthiopropanoyl)-2-DL-piperidinecarboxaldehyde is obtained.

EXAMPLE 9

1-(3-Butanoylthiopropanoyl)-2-DL-pyrrolidinecarboxaldehyde

By substituting 3-(butanoylthio)propanoic acid for the 3-(acetylthio)propanoic acid in the procedure of Example 1, 3-(butanoylthio)propanoic acid p-nitrophenyl ester is obtained. By utilizing this product in the procedure of Example 2 and substituting DL-prolinol for the L-prolinol, then continuing as in Example 3, 1-(3-butanoylthiopropanoyl)-2-DL-pyrrolidinecarboxaldehyde is obtained.

EXAMPLE 10

1-(3-Acetylthiopropanoyl)-2-L-pyrrolidinecarboxaldehyde sodium bisulfite addition product A solution of sodium bisulfite (172 mg.) in water (15 ml.) is added to 1-(3-acetylthiopropanoyl-2-L-pyrrolidinecarboxaldehyde (400 mg.) and the suspension is stirred for sixteen hours at room temperature. It becomes almost a clear solution. The solution is filtered and on lyophilization a white powder is obtained (510 mg.). NMR of this material shows the absence of aldehyde proton but the presence of a new doublet at 4.9 δ $[\alpha]_D = -38.6$ (c=1.4, $H_2O$).

EXAMPLE 11

1-(3-Mercaptopropanoyl)-2-L-(hydroxymethyl)pyrrolidine 1-(3-Acetylthiopropanoyl)-2-L-hydroxymethylpyrrolidine (1 g.) is dissolved in 5.5 M ammonium hydroxide (6 ml.) and the solution is kept at room temperature under argon for thirty minutes. The mixture is concentrated in vacuo, then passed through a column of Dowex 50 ion exchange resin (hydrogen form) and washed with water. The water is removed by freeze drying; yield 770 mg., $R_f$0.5 ($CHCl_3$:MeOH, 9:1, silica gel) $[\alpha]_D^{25} -53.3$ (0.1, $CHCl_3$).

EXAMPLE 12

1,1'-[Dithiobis(3-propanoyl)]-bis-2-L-(hydroxymethyl)pyrrolidine 1-(3-Mercaptopropanoyl)-2-L-hydroxymethylpyrrolidine (0.95 g.) is dissolved in water (20 ml.) and the pH adjusted to 6.5 with N-sodium hydroxide. An ethanolic solution of iodine is added dropwise until a permanent yellow color appears. The color is discharged with a drop of sodium thiosulfate and the solution is passed through a column of Dowex 50 ion exchange resin. The aqueous solution is concentrated to dryness to yield 1,1'-[dithiobis(3-propanoyl)]-bis-2-L-(hydroxymethyl)pyrrolidine.

EXAMPLE 13

1,1'-[Dithiobis-(3-propanoyl)]-bis-2-L-pyrrolidinecarboxaldehyde

By substituting 1,1'-[dithiobis(3-propanoyl)]-bis-2-L-hydroxymethylpyrrolidine for the 1-[3-acetylthiopropanoyl-2-(L-hydroxymethyl)pyrrolidine in the procedure of Example 3 1,1'-[dithiobis-(3-propanoyl)]-bis-2-L-pyrrolidinecarboxaldehyde is obtained.

EXAMPLE 14

1-(3-Mercaptopropanoyl)-2-L-pyrrolidinecarboxaldehyde 1-(3-Acetylthiopropanoyl)-2-L-pyrrolidinecarboxaldehyde (1 g.) is dissolved in a mixture of methanol (5 ml.) and 2 N sodium hydroxide (5 ml.) under argon. After thirty minutes the reaction mixture is diluted with 2 N hydrochloric acid (20 ml.) and extracted with ethyl acetate. The organic phase is dried over magnesium sulfate and concentrated to dryness in vacuo to yield 1-(3-mercaptopropanoyl)-2-L-pyrrolidinecarboxaldehyde. This material should be used as soon as it is prepared because it is unstable.

EXAMPLE 15

1,1'-[Dithiobis-(2-methyl-3-propanoyl)]-bis-2-L-pyrrolidinecarboxaldehyde

By substituting 1-(3-acetylthio-2-methylpropanoyl)-2-L-(hydroxymethyl)pyrrolidine for the 1-(3-acetylthiopropanoyl-2-L-(hydroxymethyl)pyrrolidine in the procedure of Example 11, and then submitting the product to the procedure of Examples 12 and 13, 1,1'-[dithiobis-(2-methyl-3-propanoyl)]-bis-2-L-pyrrolidinecarboxaldehyde is obtained.

EXAMPLE 16

1-(3-Mercapto-2-methylpropanoyl)-2-L-pyrrolidine carboxaldehyde

By substituting 1-(3-acetylthio-2-methylpropanoyl)-2-L-pyrrolidinecarboxaldehyde for the 1-(3-acetylthiopropanoyl)-2-L-pyrrolidinecarboxaldehyde in the procedure of Example 14, 1-(3-mercapto-2-methylpropanoyl)-2-L-pyrrolidinecarboxaldehyde is obtained.

EXAMPLE 17

1-Benzyloxycarbonyl-4-benzyl-2-L-pyrrolidinecarboxaldehyde dimethyl acetal (a) 1-Benzyloxycarbonyl-4-benzyloxy-L-proline (4.55 g.) [obtained from 4-benzyloxyproline [Biochem. Biophys. Acta 303, 198 (1973)] and benzyloxycarbonyl chloride] and 3,5-dimethylpyrazole (1.15 g.) are dissolved in chloroform (200 ml.). Dicyclohexylcarbodiimide (2.06 g.) is added and the mixture is stirred in an ice-salt bath for one hour and at room temperature for 16 hours. The precipitate is filtered and the filtrate is concentrated to dryness. The residue is dissolved in ethyl acetate, washed with N-hydrochloric acid and water. The organic layer is dried and concentrated to dryness in vacuo to yield 1-benzyloxycarbonyl-4-benzyloxy-L-proline-3,5-dimethylpyrazolide.

(b) The dimethylpyrazolide (5.3 g.) dissolved in tetrahydrofuran (200 ml.) is added to a suspension of lithium aluminum hydride (20 mmols.) in tetrahydrofuran (200 ml.) over a period of one hour, keeping the temperature between −15° and −20°. After stirring for another hour at this temperature, 2 N hydrochloric acid (12 ml.) is added slowly at −20° under a slow current of argon. The precipitate of aluminum hydroxide is centrifuged and the solvent is removed in vacuo. The residue is dissolved in ether, washed with water and evaporated. The residue is dissolved in absolute methanol and 0.02 ml. of concentrated hydrochloric acid is added. The mixture is stored at room temperature for three days, concentrated to dryness, the residue is dissolved in ethyl acetate and washed with saturated sodium bicarbonate and water. The organic phase is dried and concentrated to dryness in vacuo to yield 1-benzyloxycarbonyl-4-benzyl-2-L-pyrrolidinecarboxaldehyde dimethyl acetal.

EXAMPLE 18

1-(3-Acetylthiopropanoyl)-4-hydroxy-2-L-pyrrolidinecarboxaldehyde (a) 1-Benzyloxycarbonyl-4-benzyl-2-L-pyrrolidine carboxyaldehyde dimethyl acetal (4.8 g.) is dissolved in methanol (150 ml.), 10% palladium on charcoal (500 mg.) is added and the mixture is stirred under a current of hydrogen until no more carbon dioxide is evolved. The catalyst is filtered off and the filtrate is concentrated to dryness in vacuo. The residue and 3-(acetylthio)propanoic acid p-nitrophenyl ester (2.8 g.) are dissolved in dimethylformamide (20 ml.) and the mixture is stored at room temperature for sixteen hours. The solvent is removed in vacuo and the residue is chromatographed on a silica gel column using a gradient of benzene:acetone to isolate the 1-(3-acetylthiopropanoyl)-4-hydroxy-2-L-pyrrolidinecarboxaldehyde dimethyl acetal.

(b) The dimethyl acetyl of paragraph (a) is suspended in 0.1 N hydrochloric acid and the mixture is stirred at room temperature until complete hydrolysis of the acetal is obtained. The aqueous mixture is extracted with ethyl acetate, the organic phase is washed with water, dried with magnesium sulfate and concentrated to dryness in vacuo to yield 1-(3-acetylthiopropanoyl)-4-hydroxy-2-L-pyrrolidinecarboxaldehyde.

EXAMPLE 19

1-(3-Acetylthio-2-methylpropyl)-4-hydroxy-2-L-pyrrolidinecarboxaldehyde

By substituting 3-acetylthio-2-methylpropanoic acid p-nitrophenyl ester for the 3-acetylthiopropanoic acid p-nitrophenyl ester in the procedure of Example 18, 1-(3-acetylthio-2-methylpropanoyl)-4-hydroxy-2-L-pyrrolidinecarboxaldehyde is obtained.

EXAMPLE 20

1-(3-Acetylthiopropanoyl)-2-L-pyrrolidinecarboxaldehyde dimethyl acetal

A solution of 1-(3-acetylthiopropanoyl)-2-L-pyrrolidinecarboxaldehyde (1 g.) in absolute methanol (10 ml.) and 0.02 ml. of concentrated hydrochloric acid is stored at room temperature for three days. The solvent is removed in vacuo and the residue is dissolved in ethyl acetate and washed with sodium bicarbonate and water. The organic layer is dried and concentrated to dryness to give 1-(3-acetylthiopropanoyl)-2-L-pyrrolidinecarboxaldehyde dimethyl acetal.

EXAMPLE 21

1-(3-Acetylthio-2-methylpropanoyl)-2-L-pyrrolidinecarboxyaldehyde dimethyl acetal By substituting 1-(3-acetylthio-2-methylpropanoyl)-2-L-pyrrolidinecarboxyaldehyde for the 1-(3-acetylthiopropanoyl)-2-L-pyrrolidinecarboxaldehyde in the procedure of Example 20, 1-(3-acetylthio-2-methylpropanoyl)-2-L-pyrrolidinecarboxaldehyde dimethyl acetal is obtained.

EXAMPLE 22

1-(3-Mercapto-2-methylpropanoyl)-2-L-pyrrolidinecarboxaldehyde dimethyl acetal 1-(3-Acetylthio-2-methylpropanoyl)-2-L-pyrrolidinecarboxaldehyde dimethylacetal (1 g.) is dissolved in a mixture of methanol (5 ml.) and 2 N sodium hydroxide (5 ml.). After 60 minutes, the mixture is diluted with water (30 ml.). The pH is adjusted to 5 and the mixture is extracted with ethyl acetate. The organic layer is washed, dried and concentrated to dryness to give 1-(3-mercapto-2-methylpropanoyl)-2-L-pyrrolidinecarboxaldehyde dimethyl acetal.

The following additional products are produced by the procedure of the example indicated in parenthesis utilizing the corresponding pipecolic acid and 2-(hydroxymethyl)piperidine derivatives as starting materials:

| Example | |
|---|---|
| 23 | 1-(3-Mercaptopropanoyl)-2-L-(hydroxymethyl)-piperidine (Example 11) |
| 24 | 1,1'-[Dithiobis-(3-propanoyl)]-bis-2-L-(hydroxymethyl)piperidine (Example 12) |
| 25 | 1,1'-[Dithiobis-(3-propanoyl)]-bis-2-L-piperidinecarboxaldehyde (Example 13) |
| 26 | 1-(3-Mercaptopropanoyl)-2-L-piperidinecarboxaldehyde (Example 14) |
| 27 | 1,1'-[Dithiobis-(2-methyl-3-propanoyl)]-bis-2-L-piperidinecarboxaldehyde (Example 15) |
| 28 | 1-(3-Mercapto-2-methylpropanoyl)-2-L-piperi- |

| Example | |
|---|---|
| | dinecarboxaldehyde (Example 16) |
| 29 | 1-(3-Acetylthiopropanoyl)-5-hydroxy-2-L-piperidinecarboxaldehyde (Examples 17–18) |
| 30 | 1-(3-Acetylthio-2-methylpropanoyl)-5-hydroxy-2-L-piperidinecarboxyaldehyde (Example 19) |
| 31 | 1-(3-Acetylthiopropanoly)-2-L-piperidinecarboxaldehyde dimethyl acetal (Example 20) |
| 32 | 1-(3-Acetylthio-2-methylpropanoyl)-2-L-piperidinecarboxaldehyde dimethyl acetal (Example 21) |
| 33 | 1-(3-Mercapto-2-methylpropanoyl)-2-L-piperidinecarboxaldehyde dimethyl acetal (Example 22) |
| 34 | 1-(3-Butanoylthiopropanoyl)-2-DL-piperidinecarboxaldehyde (Example 9) |
| 35 | 1-(3-Acetylthiopropanoyl)-2-L-piperidinecarboxaldehyde sodium bisulfite addition product (Example 10) |
| 36 | 1-(3-Mercapto-2-methylpropanoyl)-2-pyrrolidinecarboxaldehyde sodium bisulfite addition product (Example 10) |

EXAMPLE 37

1,1'-[Dithiobis-(3-propanoyl)]-bis-2-L-pyrrolidine carboxaldehyde sodium bisulfite addition product By substituting 1,1'-[dithiobis-(3-propanoyl)]-bis-2-L-pyrrolidine carboxaldehyde for the 1-(3-acetylthiopropanoyl)-2-L-pyrrolidine carboxaldehyde in the procedure of Example 10, 1,1'-[dithiobis-(3-propanoyl)]-bis-2-L-pyrrolidine carboxaldehyde sodium bisulfite addition product is obtained.

EXAMPLE 38

1,1'-[Dithiobis-(2-methyl-3-propanoyl)]-bis-2-pyrrolidine carboxaldehyde sodium bisulfite addition product By substituting 1,1'-[dithiobis-(2-methyl-3-propanoyl)]-bis-2-L-pyrrolidine carboxaldehyde for the 1-(3-acetylthiopropanoyl)-2-L-pyrrolidine carboxaldehyde in the procedure of Example 10, 1,1'-[dithiobis-(2-methyl-3-propanoyl)]-bis-2-pyrrolidine carboxaldehyde sodium bisulfite addition product is obtained.

EXAMPLE 39

1,1'-[Dithiobis-(2-methyl-3-propanoyl)]-bis-2-L-piperidinecarboxaldehyde sodium bisulfite addition product By substituting 1,1'-[dithiobis-(2-methyl-3-propanoyl)]-bis-2-L-piperidinecarboxaldehyde for the 1-(3-acetylthiopropanyl)-2-L-pyrrolidine carboxaldehyde in the procedure of Example 10, 1,1'-[dithiobis-(2-methyl-3-propanoyl)]-bis-2-L-piperidinecarboxaldehyde sodium bisulfite addition product is obtained.

What is claimed is:

1. A compound of the formula

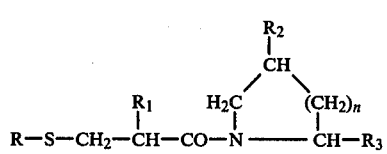

wherein R is hydrogen, lower alkanoyl of two to seven carbon atoms or

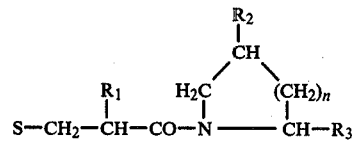

$R_1$ is hydrogen or lower alkyl of one to seven carbon atoms;
$R_2$ is hydrogen or hydroxy;
$R_3$ is hydroxymethyl, di(lower alkoxy)methyl or formyl;
n is 1 or 2;
and when $R_3$ is formyl monovalent metal bisulfate addition products thereof.

2. A compound as in claim 1 wherein n is 1.
3. A compound as in claim 1 wherein n is 2.
4. A compound as in claim 1 wherein R is acetyl.
5. A compound as in claim 1 wherein $R_2$ is formyl.
6. A compound as in claim 1 wherein $R_2$ is hydroxymethyl.
7. A compound as in claim 2 wherein $R_2$ is formyl.
8. A compound as in claim 2 wherein $R_2$ is hydroxymethyl.
9. A compound as in claim 1 wherein R is acetyl; $R_1$ is hydrogen or lower alkyl of one to seven carbon atoms; $R_2$ is formyl; and n is 1 or 2.
10. A compound as in claim 1 wherein R is acetyl; $R_1$ is hydrogen or lower alkyl of one to seven carbon atoms; $R_2$ is hydroxymethyl and n is 1 or 2.
11. A compound as in claim 2 wherein R is acetyl.
12. A compound as in claim 2 wherein R is acetyl and $R_1$ is hydrogen.
13. A compound as in claim 2 wherein R is acetyl and $R_1$ is methyl.
14. A compound as in claim 12 having the name 1-(3-acetylthiopropanoyl)-2-L-pyrrolidinecarboxaldehyde.
15. A compound as in claim 13 having the name 1-(3-acetylthio-2-methylpropanoyl)-2-L-pyrrolidinecarboxaldehyde.
16. A compound as in claim 2 wherein R and $R_1$ each is hydrogen.
17. A compound as in claim 2 wherein R is hydrogen and $R_1$ is methyl.
18. A compound as in claim 16 having the name 1-(3-mercaptopropanoyl)-2-L-pyrrolidinecarboxaldehyde.
19. A compound as in claim 17 having the name 1-(3-mercapto-2-methylpropanoyl)-2-L-pyrrolidine-carboxaldehyde.
20. A compound as in claim 1 wherein R is

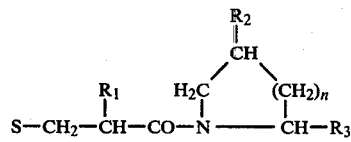

21. A compound as in claim 20 having the name 1,1'-[dithiobis-(2-methyl-3-propanoyl)]-bis-2-L-pyrrolidinecarboxaldehyde.

* * * * *